(12) United States Patent
Mentak

(10) Patent No.: US 8,247,511 B2
(45) Date of Patent: *Aug. 21, 2012

(54) WATER PLASTICIZED HIGH REFRACTIVE INDEX POLYMER FOR OPHTHALMIC APPLICATIONS

(75) Inventor: Khalid Mentak, San Ramon, CA (US)

(73) Assignee: Advanced Vision Science, Inc., Goleta, CA (US)

( * ) Notice: Subject to any disclaimer, the term of this patent is extended or adjusted under 35 U.S.C. 154(b) by 996 days.

This patent is subject to a terminal disclaimer.

(21) Appl. No.: 11/494,911

(22) Filed: Jul. 28, 2006

(65) Prior Publication Data

US 2007/0010883 A1    Jan. 11, 2007

Related U.S. Application Data

(60) Continuation-in-part of application No. 09/917,971, filed on Jul. 30, 2001, now Pat. No. 7,083,645, which is a division of application No. 09/358,757, filed on Jul. 22, 1999, now Pat. No. 6,281,319.

(60) Provisional application No. 60/128,751, filed on Apr. 12, 1999.

(51) Int. Cl.
C08F 118/02    (2006.01)
C08F 2/46      (2006.01)

(52) U.S. Cl. ....... 526/347; 526/320; 526/329; 623/6.11; 623/6.58

(58) Field of Classification Search .......... 623/6.58, 623/6.11; 526/320, 329.2, 347
See application file for complete search history.

(56) References Cited

U.S. PATENT DOCUMENTS

| | | | |
|---|---|---|---|
| 4,228,269 A | 10/1980 | Loshaek et al. | |
| 4,327,202 A | 4/1982 | Foley, Jr. | |
| 4,528,301 A | 7/1985 | Upchurch et al. | |
| 4,619,662 A | 10/1986 | Juergens, Jr. | |
| 4,715,373 A | 12/1987 | Mazzocco et al. | |
| 4,731,079 A * | 3/1988 | Stoy ............................. | 623/6.58 |
| 4,834,750 A | 5/1989 | Gupta | |
| 5,093,408 A | 3/1992 | Jung et al. | |
| 5,132,384 A | 7/1992 | Matsuda et al. | |
| 5,217,491 A | 6/1993 | Vanderbilt | |
| 5,290,892 A | 3/1994 | Namdaran et al. | |
| 5,326,506 A | 7/1994 | Vanderbilt | |
| 5,331,073 A | 7/1994 | Weinschenk, III et al. | |
| 5,359,021 A | 10/1994 | Weinschenk, III et al. | |
| 5,433,746 A | 7/1995 | Namdaran et al. | |
| 5,480,950 A | 1/1996 | Wang et al. | |
| 5,693,095 A | 12/1997 | Freeman et al. | |
| 5,776,191 A | 7/1998 | Mazzocco | |
| 6,150,479 A | 11/2000 | Klemarczyk et al. | |
| 6,201,089 B1 | 3/2001 | Carter | |
| 6,265,465 B1 | 7/2001 | Benz et al. | |
| 6,281,319 B1 | 8/2001 | Mentak | |
| 6,329,485 B1 * | 12/2001 | Vanderbilt .................. | 526/318.1 |
| 7,083,645 B2 * | 8/2006 | Mentak ....................... | 623/6.58 |

FOREIGN PATENT DOCUMENTS

| | | |
|---|---|---|
| EP | 0485197 | 5/1992 |
| EP | 0485197 | 10/1996 |
| GB | 2171106 | 8/1986 |
| WO | WO 96/40303 | 12/1996 |
| WO | WO 97/24382 | 7/1997 |
| WO | WO 99/07756 | 2/1999 |
| WO | WO 00/34804 | 6/2000 |
| WO | WO 00/61646 | 10/2000 |
| WO | WO01/18078 | 3/2001 |
| WO | WO01/18079 | 3/2001 |
| WO | WO 2007/142782 | 12/2007 |

OTHER PUBLICATIONS

Alcon® Laboratories, Inc., "All About Cataracts, The AcrySof® IOL Story", 1996, 2 pages, downloaded from http://www.alconlabs.com.
Martin, Robert G. et al., Foldable Intraocular Lenses, Douglas D. Koch, M.D., Ch. 8, pp. 167-177, "Alcon AcrySof™ Acrylic Intraocular Lenses", Slack, Inc., 1993.
International Search Report for PCT/US2007/016931 filed Jul. 27, 2007, mailed Feb. 11, 2008, 11 pgs.

* cited by examiner

*Primary Examiner* — Ling Choi
*Assistant Examiner* — Chun-Cheng Wang
(74) *Attorney, Agent, or Firm* — Squire Sanders (US) LLP

(57) ABSTRACT

The current invention provides a method of forming a foldable intraocular having a high refractive index from a copolymer comprising a first monomer comprising an aryl acrylate or an aryl methacrylate; a second monomer comprising an aromatic ring comprising a substituent having one ethylenic unsaturation, provided that the second monomer is not an aryl acryate or aryl methacrylate, and a third monomer comprising one ethylenic unsaturation that, if polymerized into a homopolymer, forms a high water content hydrogel; and, optionally, a cross-linking agent.

12 Claims, No Drawings

WATER PLASTICIZED HIGH REFRACTIVE INDEX POLYMER FOR OPHTHALMIC APPLICATIONS

RELATED APPLICATIONS

This application is a continuation-in-part of U.S. patent application Ser. No. 09/917,971, filed 30 Jul. 2001 now U.S. Pat. No. 7,083,645, which was a divisional of U.S. patent application Ser. No. 09/358,757, filed 22 Jul. 1999 now U.S. Pat. No. 6,281,319, which in turn claims the benefit of U.S. Provisional Patent Application Ser. No. 60/128,751, filed 12 Apr. 1999.

FIELD

This application relates to the field of organic chemistry, polymer chemistry, materials science and ophthalmic devices. In particular, this invention relates to acrylic copolymers and foldable intraocular lenses (foldable IOLs) made thereof.

BACKGROUND OF INVENTION

With recent advances in small-incision cataract surgery, increased emphasis has been placed on developing artificial ophthalmic lenses made of soft, pliable polymers whereby the lens can be folded and implanted in the eye through the same incision used to remove the natural lens. One of the primary classes of polymers found to achieve this objective is hydrogels.

Hydrogel materials are rigid when dry but can be hydrated with large amounts of water (generally 20-70% by weight) become soft and pliable. However, the hydration process tends to the refractive index of the hydrated polymer. For example, currently recognized hydrogels have a refractive index that is generally less than about 1.48. In addition to adversely affecting refractive index, the absorbed water also significantly increases the diameter and thickness of the IOLs, for example, by as much as about 15 percent.

U.S. Pat. No. 5,290,892 (Namdaran et al.), U.S. Pat. No. 5,331,073 (Weinschenk, III et al.), and U.S. Pat. No. 5,693,095 (Freeman et al.), each of which is incorporated by reference as if fully set forth herein, discuss forming foldable lenses from ethoxyaryl (meth)acrylate with a crosslinker or with a second acrylate monomer and crosslinker. The resulting polymer is soft and foldable and the patents further discuss mold-forming the polymer into lenses. U.S. Pat. No. 5,433,746 to Namdaran et al., which is also incorporated by reference as if fully set forth herein, discloses forming flexible intraocular lenses by molding polymeric materials which have a relatively low glass transition temperature. Such molding requires specialized equipment and expensive customized molds. In addition, the resulting molded lenses tend to have poor surface quality since they generally cannot be polished. To ameliorate this problem U.S. Pat. No. 5,331,073 discusses forming lenses from a soft/foldable material by machining the lenses at cryogenic temperatures, a cumbersome and expensive process.

What is needed is a polymer that in its unhydrated state can be machined using conventional technology and in its hydrated state is soft, foldable and has a high refractive index. The current invention provides such a polymer and a method of manufacturing a foldable IOL from it.

SUMMARY OF THE INVENTION

Thus, an aspect of the present invention is a method of manufacturing an intraocular lens comprising:

providing a rigid copolymer comprising:
  a first monomer comprising an aryl acrylate or an aryl methacrylate;
  a second monomer comprising an aromatic ring comprising a substituent having one ethylenic unsaturation, provided that the second monomer is not an aryl acryate or aryl methacrylate; and,
  a third monomer comprising one ethylenic unsaturation that, if polymerized into a homopolymer, forms a high water content hydrogel;
  optionally, a cross-linking agent;
machining the rigid copolymer into a rigid intraocular lens having desired dimensions and hydrating the rigid intraocular lens to form a foldable intraocular lens, wherein the foldable intraocular lens has an equilibrium water concentration of from about 1.5 wt % to about 10 wt % and a refractive index greater than about 1.50.

In an aspect of this invention, the foldable intraocular lens has an equilibrium water content from about 2 wt % to about 8 wt %.

In an aspect of this invention, the foldable intraocular lens has an equilibrium water content of about 4 wt %.

In an aspect of this invention, the method further comprises a UV blocker.

In an aspect of this invention, the method further comprises a blue light blocker.

In an aspect of this invention, the intraocular lens is a 20 diopter lens and has a central thickness less than about 0.4 mm.

In an aspect of this invention, the rigid intraocular lens is hydrated by: placing the lens in an aqueous solution;
gradually increasing the temperature of the aqueous solution to about 40° C.;
holding the temperature of the aqueous solution at about 40° C. for about 10 minutes;
gradually increasing the temperature of the aqueous solution to about 60° C.;
holding the temperature of the aqueous solution at about 60° C. for about one hour; and,
gradually decreasing the temperature of the aqueous solution to about room temperature.

In an aspect of this invention, the rigid intraocular lens is hydrated by placing it in an aqueous solution, gradually increasing the temperature of the aqueous solution to 50° C., holding the temperature at 50° C. for about 24 hours and then gradually decreasing the temperature to about room temperature.

In an aspect of this invention machining the rigid intraocular lens comprises lathe cutting the lens from a rigid sheet or rod of the copolymer and polishing the cut lens.

In an aspect of this invention the first monomer is selected from the group consisting of ethylene glycol phenyl ether acrylate (EGPEA), poly(ethylene glycol) phenyl ether acrylate ((polyEG)PEA), phenyl methacrylate, 2-ethylphenyl methacrylate, 2-ethylphenyl acrylate, hexylphenyl methacrylate, hexylphenyl acrylate, benzyl methacrylate, 2-phenylethyl methacrylate, 4-methylphenyl methacrylate, 4-methylbenzyl methacrylate, 2-(2-methylphenyl )ethyl methacrylate, 2-(3-methylphenyl )ethyl methacrylate, 2-(4-methylphenyl) ethyl methacrylate, 2-(4-propylphenyl)ethyl methacrylate. 2-(4-(1-methylethyl)pheny)ethyl methacrylate, 2-(4-methoxyphenyl)ethyl methacrylate, 2-(4-cyclohexylpheny)ethyl methacrylate, 2-(2-chlorophenyl)ethyl methacrylate, 2-(3-chlorophenyl)ethyl methacrylate, 2-(4-chlorophenyl)ethyl methacrylate, 2-(4-bromophenyl)ethyl methacrylate, 2-(3-phenylphenyl)ethyl methacrylate, 2-(4-phenylphenyl)ethyl methacrylate) or 2-(4-benzylphenyl)ethyl methacrylate.

In an aspect of this invention, the first monomer is selected from the group consisting of EGPEA and (polyEG)PEA.

In an aspect of this invention, the second monomer is selected from the group consisting of chlorostyrene and styrene.

In an aspect of this invention, the second monomer is styrene.

In an aspect of this invention, the third monomer is selected from the group consisiting of hydroxyethyl methacrylate (HEMA), hydroxyethoxyethyl methacrylate (HEEMA), hydroxydiethoxyethyl methacrylate, methoxyethyl methacrylate, methoxyethoxyethyl methacrylate, methoxydiethoxyethyl methacrylate, N-vinyl-2-pyrrolidone, methacrylic acid and vinyl alcohol.

In an aspect of this invention, the third monomer is selected from the group consisting of hydroxyethyl methacrylate (HEMA), hydroxyethoxyethyl methacrylate (HEEMA).

In an aspect of this invention, if opted, the cross-linking agent is selected from the group consisting of a divinyl compound, a vinyl ester of an acrylate or methacrylate, an allyl ester of an acrylate or methacrylate, a diacrylate, a dimethacrylate or an acrylate/methacrylate.

In an aspect of this invention, the cross-linking agent is selected from the group consisting of ethylene glycol dimethacrylate (EGDM), diethylene glycol dimethacrylate, polyethylene glycol dimethacrylate, 1-3-propanedioldimethacrylate, 1,6-hexanediol dimethacrylate, 1,3-butanediol dimethacrylate and 1,4-butanediol dimethacrylate.

In an aspect of this invention, the cross-linking agent is ethylene glycol dimethacrylate.

DETAILED DESCRIPTION

Brief Description of the Tables

Table 1 shows the composition of various copolymers of this invention and provides some physical characteristics of the copolymers.

Table 2 shows some materials of which intraocular devises are currently manufactured and likewise provides some of their physical characteristics by way of comparison with the copolymers in Table 1.

Table 3 shows the dimensional stability of the copolymer of this invention when taken from the dry state to the hydrated state.

Discussion

As used herein, "about," when referring to numerical values or ranges means that the given value or range is not absolute but may vary by as much as ±15%.

The current invention relates to foldable, high refractive index polymers that can be machined using lathe cutting and other conventional techniques such as those used in the manufacture of polymethyl methacrylate (PMMA) lenses to form IOLs. The polymers should be useful for the manufacture of ophthalmic devices such as contact lenses, keratoprostheses, intracorneal lenses (ICL) and corneal rings or inlays, etc. In particular they are useful for the manufacture of IOLs.

An advantageous property of the polymers of this invention is that they are hard enough in their unhydrated state to machine at room temperature but can be hydrated to provide soft, foldable IOLs having high refractive indices. Further, they can be hydrated to a suitably flexible state using a relatively small amount of water. The use of minimal water ameliorates the adverse effects of hydration on the polymer's mechanical and optical properties such as those observed with other high water content hydrogel lens materials. Dimensional changes in the end product are also minimized.

Another advantage of the polymers of the present invention is that lenses can be tumble polished to provide smooth and rounded edges. This is facilitated by the relatively high glass transition temperature (Tg) of the material as well as other mechanical properties.

The polymers of the present invention are copolymers comprising at least three monomers. One of the monomers is an aryl acrylate or methacrylate (acrylates and methacrylates are referred to herein by the shorthand designation (meth) acrylate), one is a non-(meth)acrylate aryl group-containing monomer wherein the aryl group is substituted with an ethylenic unsaturation (and may be further substituted as well) and the third is a monomer containing one ethylenic unsaturation and which, as a homopolymer, forms a high water content hydrogel. The copolymer may be cross-linked if desired.

As used herein an "ethylenic unsaturation" simply refers to an aliphatic —C=C— moiety which may occur anywhere in the molecule but preferably at present is at a terminal position, i.e., is a —C=CH$_2$ group.

As used herein, reference to the weight percent (wt %) of monomers refers to the percentage calculated as the weight of the monomer in the polymerization reaction mixture divided by the total weight of monomers in the reaction. When polymerized, the wt % of the constitutional unit based on the particular monomer will be slightly different than preceding but the difference is inconsequential. As a convenient shorthand for this information, the phrase "in the copolymer" will be used when discussing monomer weight percentages but it is understood that the number is actually derived from the foregoing.

A copolymer of this invention may be a random or block copolymer.

The proportion of each monomer in the copolymer is selected to provide a substantially rigid polymer having a glass transition temperature of at least about normal room temperature. It is presently preferred that each of the three monomers is present in the copolymer in an amount of at least about 10 wt %, more preferably, at least about 20 wt %. In a presently preferred embodiment, the copolymer comprises:

a) at least about 20 wt % of a first monomer such as, without limitation, ethylene glycol phenyl ether acrylate or polyethylene glycol phenyl ether acrylate;

b) at least about 10 wt % of a second monomer such as, without limitation, styrene or substituted styrene;

c) at least about 10 wt % of a third monomer such as, without limitation, hydroxy ethyl methacrylate, hydroxyethoxy ethyl methacrylate, or methacrylic acid; and, d) less than about 10 wt % of a crosslinking agent such as a diacrylate or a dimethacrylate.

The copolymer resulting from the polymerization of the above monomers should, when hydrated, be foldable at or above normal room temperature, i.e., above about 15° C. and should have a refractive index greater than about 1.50.

As used herein, "aryl" refers to a carbocyclic (all carbon) ring or two or more fused (rings that share two adjacent carbon atoms) carbocyclic rings that have a fully delocalized pi-electron system. For the purpose of this invention, "aryl" also refers to a heteroaryl ring, that is, a ring or two or more fused rings at least one of which contains one or more heteroatoms selected from the group consisting of nitrogen, oxygen and sulfur wherein the ring or rings likewise have a fully delocalized pi-electron system. Examples of carbocyclic aryl groups include, without limitation, benzene, naphthalene and azulene. Examples of heterocyclic aryl rings include, but are not limited to, furan, thiophene, pyrrole, thiazole, imidazole, oxazole, isoxazole, isothiazole, triazole, thiadiazole, pyridine, pyrimidine, pyrazine, and triazine, The aryl (meth)acrylates monomers of this invention have the formula

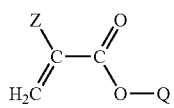

wherein Z is —H or —CH₃ and Q is an entity comprising at least one aryl group.

For example, Q may be, without limitation, ethylene glycol phenyl ether, poly(ethylene glycol phenyl ether), phenyl, 2-ethylphenyl, hexylphenyl, benzyl, 2-phenylethyl, 4-methylphenyl, 4-methylbenzyl, 2-(2-methyphenyl)ethyl, 2-(3-methylphenyl)ethyl, 2(4-methylphenyl)ethyl, 2-(4-propylphenyl)ethyl, 2-(4-(1-methylethyl)phenyl)ethyl, 2-(4-methoxyphenyl)ethyl, 2-(4-cyclohexylphenyl)ethyl, 2-(2-chlorophenyl)ethyl, 2-(3-chlorophenyl)ethyl 2-(4-chlorophenyl)ethyl, 2-(4-bromophenyl)ethyl, 2-(3-phenylphenyl)ethyl, 2-(4-phenylphenyl) ethyl) or 2-(4-benzylphenyl)ethyl.

More specifically, suitable (meth)acrylate monomers include, without limitation: ethylene glycol phenyl ether acrylate (EGPEA), poly(ethylene glycol) phenyl ether acrylate ((polyEG)PEA), phenyl methacrylate, 2-ethylphenyl methacrylate, 2-ethylphenyl acrylate, hexylphenyl methacrylate, hexylphenyl acrylate, benzyl methacrylate, 2-phenylethyl methacrylate, 4-methylphenyl methacrylate, 4-methylbenzyl methacrylate, 2-(2-methylphenyl)ethyl methacrylate, 2-(3-methylphenyl)ethyl methacrylate, 2-(4-methylphenyl) ethyl methacrylate, 2-(4-propylphenyl)ethyl methacrylate. 2-(4-(1-methylethyl)pheny)ethyl methacrylate, 2-(4-methoxyphenyl)ethylmethacrylate, 2-(4-cyclohexylpheny)ethyl methacrylate, 2-(2-chlorophenyl)ethyl methacrylate, 2-(3-chlorophenyl)ethyl methacrylate, 2-(4-chlorophenyl)ethyl methacrylate, 2-(4-bromophenyl)ethyl methacrylate, 2-(3-phenylphenyl)ethyl methacrylate, 2-(4-phenylphenyl)ethyl methacrylate) or 2-(4-benzylphenyl)ethyl methacrylate. Based on the disclosure herein, those skilled in the art will recognize other aryl (meth)acrylates that can be used to prepare the copolymers herein; all such aryl (meth)acrylates are within the scope of this invention. EGPEA and (polyEG)PEA are presently preferred aryl (meth)acrylates.

The first monomer is present in the polymer in an amount sufficient to provide high refractive index, moderate water uptake, and enhanced backbone rigidity. Preferably, the first monomer comprises at least about 10 wt % of the composition; more preferably, at least about 20 wt % and, presently most preferably, at least about 30 wt %. The amount of the first monomer should also be sufficient to avoid an undesirably low glass transition temperature in the resulting copolymer. Preferably, the first monomer comprises less than about 60 wt % of the copolymer; more preferably, less than about 50 wt % and presently most preferably, less than about 45 wt %.

Those skilled in the art will recognize, based on the disclosure herein, other monomers that may constitute the first monomer of a copolymer of this invention; all such monomers are within the scope of this invention.

The second monomer comprises an aryl group that is substituted by at least a group having an ethylenic unstaturation but the monomer is not an aryl meth(acrylate). These monomers have the formula:

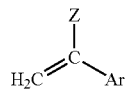

wherein Z is —H or —CH₃, and Ar is a substituted or unsubstituted aryl group.

An example of a suitable second monomer is optionally substituted styrene. If substituted, the substituent is selected from the group consisting of halogen (Br, Cl and/or F), lower alkyl (e.g. methyl, ethyl, propyl, butyl, isopropyl) and/or lower alkoxy groups.

As used herein, "alkyl" refers to a straight or branched chain fully saturated (no double or triple bonds) hydrocarbon (carbon and hydrogen only) group. Examples of alkyl groups include, but are not limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, and cyclohexyl. As used herein, "alkyl" includes "alkylene" groups, which refer to straight or branched fully saturated hydrocarbon groups having two rather than one open valences for bonding to other groups. Examples of alkylene groups include, but are not limited to methylene, —CH₂—, ethylene, —CH₂CH₂—, propylene, —CH₂CH₂CH₂—, n-butylene, —CH₂CH₂CH₂CH₂—, sec-butylene, —CH₂CH₂CH(CH₃)— and the like. For the purposes of this invention, "aliphatic" is considered synonymous with "alkyl."

As used herein, "alkoxy" refers to an —O-alkyl group.

A presently preferred second monomer is chlorostyrene and presently most preferred is styrene itself.

The second monomer is present in the copolymer in an amount sufficient to increase the glass transition temperature of the resulting copolymer to a desired working temperature. Without being held to any particular theory, it is believed that the second monomer also provides a higher refractive index and hydrophobicity due to its aromatic ring. Preferably, the second monomer comprises at least about 10 wt % of the copolymer; more preferably at least about 15 wt % and most preferably at present, at least about 20 wt %. The second monomer should be present in an amount that achieves the foregoing objectives but does not adversely affect the refractive index, optical clarity, or other desirable properties of the copolymer. Preferably, the second monomer comprises less than about 60 wt % of the copolymer; more preferably less than about 40 wt % and; most preferably at present, less than about 30 wt %.

Those skilled in the art will recognize, based on the disclosure herein, other polymers that may constitute the second polymer of a copolymer of this invention; all such polymers are within the scope of this invention.

The third monomer comprises a compound that contains one ethylenic unsaturation so that it can be included in the polymer backbone and, further, as a homopolymer, can form a high water content hydrogel. Preferably at present, the third monomer comprises a methacrylate without an aromatic substituent. Suitable third monomers include, without limitation, hydroxyethyl methacrylate (HEMA), hyd roxyethoxyethyl methacrylate (HEEMA), hydroxydiethoxyethyl methacrylate, methoxyethyl methacrylate, methoxyethoxyethyl methacrylate, methoxydiethoxyethyl methacrylate, N-vinyl-2-pyrrolidone, methacrylic acid and vinyl alcohol (which may be incorporated into the copolymer as vinyl acetate and then hydrolyzed). Those skilled in this art will recognize other third monomers based on the disclosure herein; all such monomers are within the scope of this invention. At present, HEMA and HEEMA are preferred third monomers.

The third monomer is present in an amount sufficient to render the resulting copolymer hydratable at the level of about 10% or less. Preferably, the third monomer is present in at least about 10 wt % of the composition; more preferably at least about 20 wt % and, most preferably at present, at least about 25 wt %. The third monomer should be present in an amount low enough to avoid significant expansion of the copolymer on hydration. Preferably, the third monomer comprises less than about 60 wt %, more preferably less than about 50 wt % and, most preferably at present, less than about 40 wt % of the copolymer.

The copolymer may also include a crosslinking agent. Crosslinking agents for the purpose of this invention comprise compounds with two or more sites of ethylenic unsaturation. Preferably at present, both ethylenic unsaturation sites are at terminal positions on the crosslinking agent. The crosslinking agent may be, for example without limitation, a divinyl compound, a vinyl or allyl ester of a (methacrylate), a diacrylate, a dimethacrylate or a combiation of acrylate and methacrylate. Preferably at present, the crosslinking agent comprises a diacrylate, a dimethacrylate or an acrylate/methacrylate, that is an agent wherein one of the ethylenic unsaturations is contained in an acryate and another in a methacrylate. Particularly preferred crosslinking agents at present have the following formula:

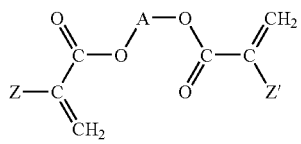

wherein Z and Z' are independently hydrogen or —$CH_3$ and A is an optionally substituted alkyl, cycloalkyl or aryl group.

Examples of crosslinking agents of this invention include, without limitation, ethylene glycol dimethacrylate (EGDM), diethylene glycol dimethacrylate, polyethylene glycol dimethacrylate, 1-3-propanedioldimethacrylate, 1,6-hexanediol dimethacrylate, 1,3-butanediol dimethacrylate and 1,4-butanediol dimethacrylate. Most preferred at presnt is ethylene glycol dimethacrylate.

The crosslinking agent should be present in an amount sufficient to permit the hydrated copolymer to return to its original shape after being folded. Preferably, the crosslinking agent comprises at least about 1.0 wt % of the composition; more preferably, at least about 3.0 wt %. Conversely, the crosslinking agent should be present in an amount low enough to avoid making the copolymer too rigid or brittle. Preferably, the crosslinking agent comprises less than about 10 wt % of the copolymer, more preferably at present less than about 5 wt %.

One skilled in the art will appreciate that additives such as ultraviolet (UV) blocking agents, blue light blocking agents, etc. optionally may be added to the copolymer-containing composition depending upon the intended application. Such may be added during the polymerization reaction any may in fact contain an ethylenic unsaturation such that it becomes incorporated into the backbone of the copolymer or it may be added after polymerization and before being formed into a machinable configuration. Representative UV absorbing materials include those disclosed, for example, in column 5, lines 3-29 of U.S. Pat. No. 5,433,746 to Namdaran et al., which is incorporated by reference as if fully set forth herein. Suitable UV absorbers include, for example without limitation, benzophenone, vinyl benzophenone, and benzotriazole. When employed, the UV absorbing material is preferably added in a concentration less than about 1 percent based on the total weight of the copolymer.

The copolymers of the invention may be produced using conventional polymerization techniques. For example, the monomers can be blended together and heated to an elevated temperature to facilitate the polymerization reaction. Catalysts and/or initiators selected well-known to those skilled in the polymerization art, may be included in the monomer mix in order to promote, and/or increase the rate of, the polymerization reaction. Examples of such catalysts/initiators include, without limitation, free radical initiators such as 2-2'-azobisisobutyronitrile (AIBN), benzoyl peroxide, acetyl peroxide, lauryl peroxide and t-butyl peroxide. At present, 2-2'-azobisisobutyronitrile (AIBN) is a preferred initiator.

A method of manufacturing ophthalmic devices using a copolymer of this invention may comprise the following: a copolymer, which has a glass transition temperature greater than about normal room temperature, i.e., about 15° C. or 60° F., and a refractive index greater than about 1.50; that is, a copolymer of this invention, is provided. The copolymer, in its unhydrated, i.e., rigid, state is formed into a rigid ophthalmic device having the desired dimensions. The ophthalmic device is then hydrated to form a foldable ophthalmic device. Preferably, the hydrated copolymer has an equilibrium water concentration less than about 10 wt % and a refractive index greater than about 1.50.

A copolymer of the present invention may be formed into the shape of sheet or rod for the purpose of manufacturing an ophthalmic device of this invention. The ophthalmic device is cut to a desired dimension and diopter from a sheet or the rod of copolymer using standard lathe cutting techniques at room temperature and the is polished, likewise using standard techniques such as tumble polishing.

The ophthalmic device, for example and preferably at present an IOL, is then hydrated. This may be achieved by soaking it in an aqueous solution (water or saline), preferably at an elevated temperature (e.g. between 20-100° C.), for a sufficient time to allow the polymer to reach its equilibrium water content.

As used herein "equilibrium water content" refers to the maximum quantity of aqueous solution such as, without limitation, isotonic saline that copolymer of this invention can absorb at a given temperature, stated as a weight percent (wt %) calculated using the formula EWC (%)=$100 \times (M_h-M_d)/M_d$, wherein $M_d$ is the weight of the dry polymer and $M_h$ is the weight of the hydrated polymer. For the purposes of this invention, the equilibrium water content is the amount of water that the copolymer can contain at about body temperature, that is, about 37° C. To achieve the desired equilibrium water content for a copolymer of this invention, the copolymer, after being machined into an ophthalmic device may be placed in an aqueous solution, the temperature may be increased to about 40° C. and then held at about 40° C. for about 10 minutes. Next, the temperature may be gradually increased to about 60° C., held there for about one hour and then gradually decreased to about room temperature. It is understood that this is simply one way of achieving equilibrium water content for a polymer of this invention. Those skilled in the art will, based on the disclosure here, readily recognize other protocols for achieving equilibrium water concentration of these copolymers; all such protocols are within the scope of this invention.

As used herein, "isotonic saline" refers to a salt, normally sodium chloride, dissolved in water, the amount of salt being substantially the same as that in bodily fluids. For use in the eye, this is approximately 0.8-0.9% w/v (weight per unit volume) of sodium chloride in water. In the metric system, w/v is the same as w/w since a unit volume of water, that is one cubic centimeter, weight one gram. The isotonic saline may be buffered to match intraocular pH by the addition of boric acid and sodium borate or sodium phosphate and potassium phosphate (phosphate-buffered saline, PBS). Presently preferred isotonic saline solutions for use in the intraocular lens and method of this invention are phosphate-buffered saline, such as, without limitation, Dulbecco's buffered phosphate solution; balanced salt solutions such as, again without limitation, Hank's balanced salt solution and Earle's balanced salt solution; and blood bank saline, an approximately 0.85 to 0.9% sodium chloride solution buffered to blood pH (7.0-7.2). Numerous other physiological (i.e., isotonic) saline preparations containing a variety of additional substances are known in the art; any of them that are known or shown to be usable in the eye may be used as the isotonic solution of this invention and all such physiological saline solutions are within the scope of this invention.

An IOL or other ophthalmic device fabricated from a polymer of the present invention should not significantly change shape or dimensions when hydrated. That is, there should be no statistically significant difference between the diameter and thickness of the dry device and that of the hydrated device.

The copolymers of the invention have a unique combination of desirable characteristics: high refractive index, good mechanical properties, high glass transition temperature, optical clarity, hydratability, and foldability once hydrated. Particularly advantageous is the fact that the copolymers of this invention are foldable at or above normal room temperature (i.e., at or above about 15° C.) despite having a glass transition temperature above room temperature and also that, in the hydrated state, they have a refractive index (RI) of about 1.50 or higher.

The refractive power of a lens is a function of its shape and the inherent refractive index of the material of which it is made. In general, the higher the refractive index, the better the material, all other factors being equal. A lens made from a material having a higher refractive index can be thin and provide the same refractive power as a thicker lens made from a material having a relatively lower refractive index. Thinner lenses are easier to insert and cause less traumatic injury during surgery. Refractive indices of at least 1.50 have been attained with copolymers of the present invention.

A dry copolymer of this invention, due in part to its glass transition temperature, is rigid but not brittle. This permits cutting and polishing (i.e., machining) of objects, e.g., lenses, at room temperature rather than having to mold them or shape them at cryogenic temperatures as in the prior art. In fact, at room temperature the hydrated polymers of this invention can be bent 180 degrees without cracking.

The ability to cut and polish an ophthalmic device made from a polymer of this invention facilitates forming a lens having the minimal central thickness allowed by the refractive index of the polymer. Thus, a thinner lens can be produced from a copolymer of the invention than from material having the same refractive index but which must be molded into a desired shape. For example, a 20 diopter lens may be produced from a polymer of this invention having a central thickness less than about 0.8 mm. The thinness of the lens permits it to be inserted through an incision as small as about 2 mm, even less. This is a significant improvement over the current state of the art in the field of ophthalmic surgery where much larger incisions are generally required for lens insertion.

The glass transition temperature (Tg) of a copolymer of this invention is preferably greater than about 15° C. so that it is workable by conventional cutting and lathing techniques. That is, at room temperature, the copolymer is rigid enough to be machined. Preferably, the Tg is greater than about 15° C., more preferably greater than about 25° C., and most preferably at present, greater than about 30° C. The Tg of a copolymer of this invention may be determined using any means accepted in the art but it is noted that different techniques can lead to sometimes substantially different results. For the purposes of this invention dynamic mechanical analysis is presently preferred.

A hydrated copolymer of this invention will have an equilibrium water content (EWC) less than about 10 wt %, preferably less than about 8% wt %, even more preferably less than about 5 wt % and, most preferably at present, 4 wt % or less. More particularly, at present a hydrated copolymer of this invention has an equilibrium water concentration of from about 3 wt % to about 10 wt %, preferably from about 4 wt % to about 8 wt % and, presently most preferably, about 4 wt %. Such a low water uptake allows effective hydration without adverse affect on the mechanical or optical properties of the foldable lens. For example, at these EWC levels neither a lens's dimension nor refractive index changes significantly upon hydration. In addition, the copolymers of the invention tend to expand less than about 10 volume percent during hydration; preferably the volume percent expansion upon hydration is less than about 5%. Expansion percent is calculated by measuring the difference in dimension of standard buttons made of the copolymer before and after hydration.

An artificial lens manufactured from a copolymer of this invention may be inserted into an eye using the same 2 mm incision currently used for cataract surgery. No sutures may be required.

A method of implanting an IOL in an eye may comprise providing a hydrated IOL comprising a copolymer of this invention and injecting it into the eye by means of a syringe, preferable through an incision less than about 2 mm in length.

The lens may be inserted using a device, for example, like that described in U.S. Pat. No. 4,715,373, which is incorporated as if fully set forth herein. The shape of the fixation system used to position the IOL in the eye is not critical to this invention. The copolymers may be used in a foldable lens having a variety of fixation systems. See, for example, U.S. Pat. No. 5,776,191, which is likewise incorporated as if fully set forth herein for a discussion of fixation systems for IOLs.

EXAMPLES

Example 1

Various copolymers were prepared by mixing the following ingredients under reduced pressure: a first, second and third monomeric component, a crosslinker and a polymerizable UV blocking agent. For example without limitation, vinyl benzotriazole at a total concentration of 0.3% by weight may be used as a UV blocking agent. To initiate polymerization a free radical initiator, 2-2'-azobisisobutyronitrile (AIBN), was employed at concentration of 0.2% by weight. The monomer solution was mixed in a glass flask using a magnetic stir bar for 30 minutes. The solution was filtered through a 0.2 micron (μ) filter and injected into a sheet mold comprising two glass plates held together with spring clips and separated by a plastic gasket. The mold was then placed in a water bath for 10 hours at 60° C., removed and post-cured at 95° C. for 12 hours. A clear, hard polymer sheet was obtained.

Intraocular lenses of various diopters (5, 10, 20, and 34) were cut from the rigid plastic sheet using conventional machining techniques such as those employed in the manufacture of polymethylmethacrylate (PMMA) IOLs.

The IOLs were tumble polished for 2 days at 20° C. The polished lenses were rinsed with ultra-pure water. At this stage the IOLs are still hard and non-foldable. The IOLs were then placed in individual vials filled with saline solution. The vials were placed in a temperature controlled oven and subjected to the following conditioning cycle: increase temperature from 20° C. to 40° C. at a rate of 10° C. per hour. Hold at 40° C. for 30 minutes. Increase temperature to 60° C. at a rate of 10° C. per hour. Hold at 60° C. for 4 hours. Decrease temperature to room temperature (approximately 20° C.) at 10° C. per hour. At this point the IOLs were soft and easily foldable and had excellent optical properties. Lens dimensions (optic size, thickness, diameter) did not change significantly with hydration. The surface and edges of the samples were found to be very smooth.

The equilibrium water content was measured after hydration using gravimetric analysis. The refractive index and glass transition temperature of the lenses was also measured. The results are shown in Table 1.

into disks so the radii and dimensions of the final product may be selected in advance. Fair machinability means the material can be machined if environmental parameters can be controlled, for example, by decreasing the temperature. Poor machinability means the material tends to deform or break during lathe cutting, but it is still machinable if environmental parameters are controlled. Not machinable means the material cannot be cut with a lathe and must be formed using methods such as molding. "Foldability" refers to the ability to bend the material as much as about 180° without breaking once the material has been hydrated. Good foldability means

TABLE 1

| Formulation | 1st Monomer | 2nd Monomer | 3rd Monomer | Crosslinker | EWC (Wt %) | Machinability | Foldability | RI hydrated | Percent Expansion |
|---|---|---|---|---|---|---|---|---|---|
| 1 | 40% EGPEA | 26% styrene | 30% HEMA | 4% EGDM | 4 | Good | Fair | 1.551 | 1.5 |
| 2 | 35% EGPEA | 26% styrene | 35% HEEMA | 4% EGDM | 3.8 | Good | Fair | 1.551 | 1.5 |
| 3 | 40% poly EGPEA | 20% chlorostyrene | 36% HEMA | 4% EGDM | 3.5 | Fair | Poor | 1.552 | 1.3 |
| 4 | 43% EGPEA | 26% styrene | 27% methacrylic acid | 4%EGDM | 4.1 | Good | Fair | 1.551 | 1.8 |
| 5 | 25% poly EGPEA | 11% styrene | 60% HEMA | 4% EGDM | 12.1 | Fair | Fair | 1.523 | 5.8 |
| 6 | 40% poly EGPEA | 26% styrene | 30% HEMA | 4% EGDM | 4.0 | Good | Good | 1.551 | 0.1 |
| 7 | 45% poly EGPEA | 31% styrene | 20% HEMA | 4% EGDM | 1.3 | Good | Poor | 1.556 | 0.1 |
| 8 | 50% poly EGPEA | 36% styrene | 10% HEMA | 4% EGDM | 1.1 | Good | Poor | 1.554 | 0.1 |
| 9 | 25% poly EGPEA | 11% styrene | 60% HEEMA | 4% EGDM | 16.5 | Poor | Fair | 1.509 | 7.2 |
| 10 | 40% poly EGPEA | 26% styrene | 30% HEEMA | 4% EGDM | 9.2 | Poor | Fair | 1.514 | 6.5 |
| 11 | 45% poly EGPEA | 31% styrene | 20% HEEMA | 4% EGDM | 4.6 | Poor | Fair | 1.533 | 2.3 |
| 12 | 50% poly EGPEA | 36% styrene | 10% HEEMA | 4% EGDM | 5.3 | Poor | Fair | 1.541 | 3.6 |
| 13 | 40% poly EGPEA | 28% styrene | 30% HEMA | 2% EGDM | 5.1 | Fair | Good | 1.551 | 0.3 |
| 14 | 34% poly EGPEA | 31% styrene | 32% HEMA | 3% EGDM | 5.0 | Fair | Fair | 1.553 | 0.4 |
| 15 | 41% poly EGPEA | 26% styrene | 31% HEMA | 2% EGDM | 4.5 | Poor | Fair | 1.552 | 3.1 |
| 16 | 41% poly EGPEA | 27% styrene | 31% FIEMA | 1% EGDM | 4.8 | Poor | Fair | 1.549 | 4.6 |
| 17 | 20% poly EGPEA | 40% styrene | 40% HEMA | 1% EGDM | 3.2 | Good | Poor | 1.551 | 2.1 |
| 18 | 41% poly EGPEA | 27% chlorostyrene | 31% HEMA | 1% EGDM | 5.1 | Fair | Fair | 1.547 | 2.1 |
| 19 | 40% poly EGPEA | 26% chiorostyrene | 30%, HEMA | 4% EGDM | 4.2 | Fair | Fair | 1.551 | 0.2 |

HEMA = hydroxyethyl methacrylate
HEEMA = hydroxyethoxyethyl methacrylate
EGPEA = ethylene glycol phenylether acrylate
EGDM = ethylene glycol dimethacrylate Table 2 shows some lenses made of materials other than the copolymers of this invention for comparison purposes.

TABLE 2

| Comparative Material | EWC (Weight %) | RI | Machinability | Foldability After Hydration | Expansion % |
|---|---|---|---|---|---|
| Hydrogel 1 | 60 | 1.38 | Good | Good | 15 |
| Hydrogel 2 | 30 | 1.44 | Good | Good | II |
| Hydrogel 3 | 75 | 1.34 | Good | Good | 25 |
| Hydrogel 4 | 20 | 1.46 | Good | Good | 10 |
| Acrylic 1 | 0 | 1.54 | Not Machinable | — | 0 |
| Acrylic 2 | 0 | 1.55 | Not Machinable | — | 0 |

Hydrogel 1 = poly HEMA
Hydrogel 2 = poly (HEMA-co-MMA)
MMA = methyl methacrylate
Hydrogel 3 = poly (HEMA-co-NVP)
NVP = n-vinyl pyrrolidone
Hydrogel 4 = highly crosslinked poly (HEMA-co-MMA)
Acrylic 1 =
phenylethyl acrylate 79 weight %
methylmethacrylate 16 weight %
EGDM 5 weight %
Acrylic 2 =
2-phenoxyethyl acrylate 88 weight %
n-hexyl acrylate 10 weight %
EGDM 2 weight %

In the above table, "machinability" refers to cutting the unhydrated material with a lathe in which a diamond tool comes in contact with the material while rotating at high speed. Good machinability means the material cuts cleanly the material can be easily folded using forceps when the material is cut into a disk about the size of a standard lens. Fair foldability means a hydrated disk of the material folds when applying little force. Poor foldability means the hydrated disk folds without breaking when a greater force is applied.

Example 2

A hydration study was conducted to assess the change in dimension after complete hydration. Twenty samples of each formulation described in Example 1 were used. Samples consisted of disks 16.5 mm in diameter and 2.0 mm in thickness. The results were averaged for each formulation and are shown in Table 3.

TABLE 3

| Formulation | % Change in Diameter | % Change in Thickness |
|---|---|---|
| 1 | 0.02 ± 0.01 | 0.04 ± 0.01 |
| 2 | 0.05 ± 0.02 | 0.08 ± 0.02 |
| 3 | 0.06 ± 0.01 | 0.08 ± 0.01 |
| 4 | 0.08 ± 0.03 | 0.06 ± 0.01 |

What is claimed is:

1. A method of manufacturing an intraocular lens comprising:
providing a rigid copolymer comprising:
a first monomer selected from the group consisting of ethylene glycol phenyl ether acrylate (EGPEA) and poly(ethylene glycol) phenyl ether acrylate ((poly-EG)PEA);

a second monomer selected from the group consisting of unsubstituted styrene and substituted styrene, wherein the substituent is selected from the group consisting of bromine, chlorine, iodine, lower alkyl and lower alkoxy;

a third monomer comprising one ethylenic unsaturation that, if polymerized into a homopolymer, forms a high water content hydrogel;

optionally, a cross-linking agent;

machining the rigid copolymer into a rigid intraocular lens having desired dimensions; and, hydrating the rigid intraocular lens to form a foldable intraocular lens, wherein:

the foldable intraocular lens has an equilibrium water concentration of from about 1.5 wt % to about 10 wt % and a refractive index greater than about 1.50.

2. The method of claim 1, wherein the foldable intraocular lens has an equilibrium water content from about 2 wt % to about 8 wt %.

3. The method of claim 2, wherein the foldable intraocular lens has an equilibrium water content of about 4 wt %.

4. The method of claim 1, further comprising a UV blocker.

5. The method of claim 1, further comprising a blue light blocker.

6. The method of claim 1 wherein the intraocular lens is a 20 diopter lens and has a central thickness less than about 0.8 mm.

7. The method of claim 1, wherein machining the rigid intraocular lens comprises lathe cutting the lens from a rigid sheet or rod of the copolymer and polishing the cut lens.

8. The method of claim 1, wherein the third monomer is selected from the group consisiting of hydroxyethyl methacrylate (HEMA), hydroxyethoxyethyl methacrylate (HEEMA), hydroxydiethoxyethyl methacrylate, methoxyethyl methacrylate, methoxyethoxyethyl methacrylate, methoxydiethoxyethyl methacrylate, N-vinyl-2-pyrrolidone, methacrylic acid and vinyl alcohol.

9. The method of claim 8, wherein the third monomer is selected from the group consisting of hydroxyethyl methacrylate (HEMA), hydroxyethoxyethyl methacrylate (HEEMA).

10. The method of claim 1, wherein, if opted, the cross-linking agent is selected from the group consisting of a divinyl compound, a vinyl ester of an acrylate or methacrylate, an allyl ester of an acrylate or methacrylate, a diacrylate, a dimethacrylate or an acrylate/methacrylate.

11. The method of claim 10, wherein the cross-linking agent is selected from the group consisting of ethylene glycol dimethacrylate (EGDM), diethylene glycol dimethacrylate, polyethylene glycol dimethacrylate, 1-3-propanedioldimethacrylate, 1,6-hexanediol dimethacrylate, 1,3-butanediol dimethacrylate and 1,4-butanediol dimethacrylate.

12. The method of claim 9, wherein the cross-linking agent is ethylene glycol dimethacrylate.

* * * * *